United States Patent [19]
Ghamaty-Azimi

[11] Patent Number: 5,893,379
[45] Date of Patent: Apr. 13, 1999

[54] DENTAL FLOSSING DEVICE

[76] Inventor: Soraya Ghamaty-Azimi, 5678 Desert View Dr., La Jolla, Calif. 92037

[21] Appl. No.: 08/872,746
[22] Filed: Jun. 11, 1997
[51] Int. Cl.⁶ .................................................. A61C 15/04
[52] U.S. Cl. .............................................. 132/323; 132/327
[58] Field of Search ................................. 132/323, 321, 132/324, 325, 326, 327

[56] References Cited

U.S. PATENT DOCUMENTS

| | | | |
|---|---|---|---|
| 664,014 | 12/1900 | Coryell | 132/323 |
| 1,110,680 | 9/1914 | Gamble | 132/325 |
| 1,725,703 | 8/1929 | Eby | 132/326 |
| 2,811,162 | 10/1957 | Brody | 132/323 |
| 3,683,642 | 8/1972 | Lutrario | 63/11 |
| 5,232,002 | 8/1993 | McClallen | 132/323 |

*Primary Examiner*—Todd E. Manahan
*Assistant Examiner*—Eduardo C. Robert
*Attorney, Agent, or Firm*—Gilliam, Duncan & Harms

[57] ABSTRACT

A flossing device for flossing the teeth as part of a dental care program. The device includes a central arch made up of two legs connected by a central segment. A length of floss is secured to the free ends of the legs. Two rings sized to fit over finger tips are secured to the outside of each arch leg. Two fingers are inserted into the rings so that the floss can be brought into well controlled contact with teeth interstices. The rings may be metal rings embedded in or bonded to the arch or may be plastic rings with the arch and rings molded as a unitary structure. With plastic rings, the rings may be circumferentially divided so as to be expandable to fit larger finger tips.

6 Claims, 1 Drawing Sheet

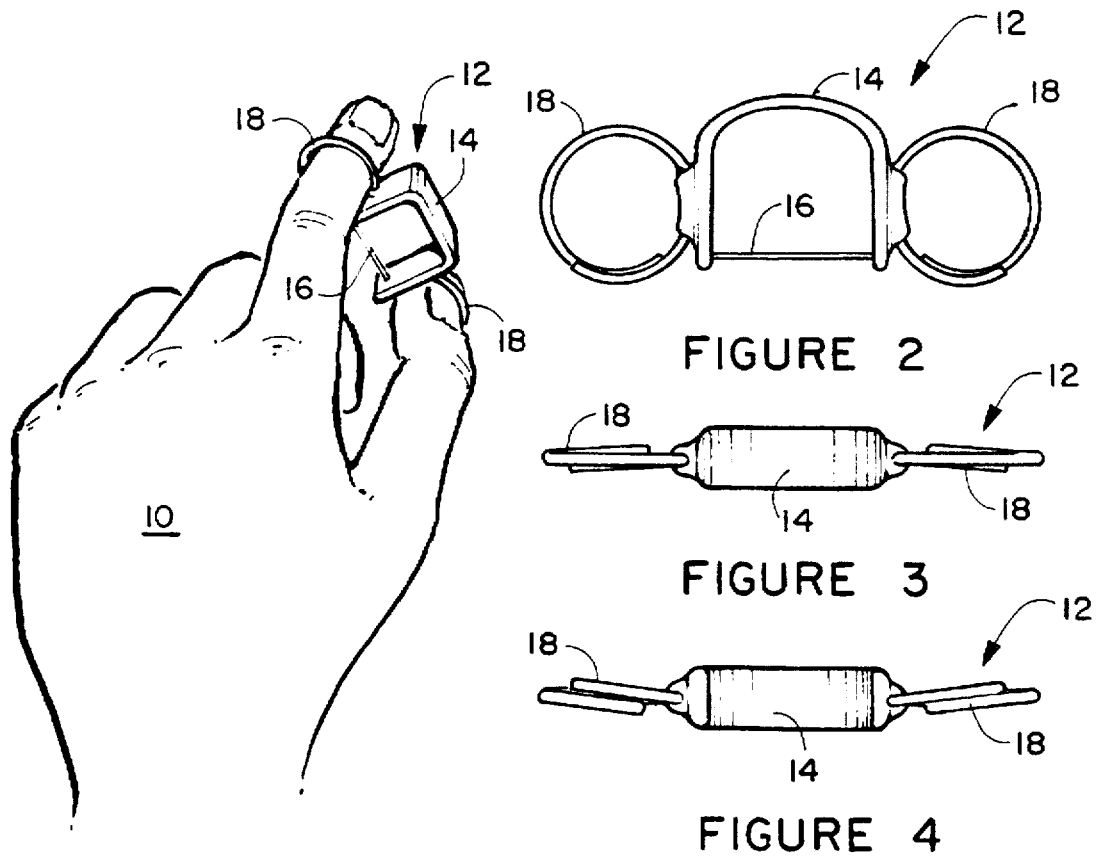
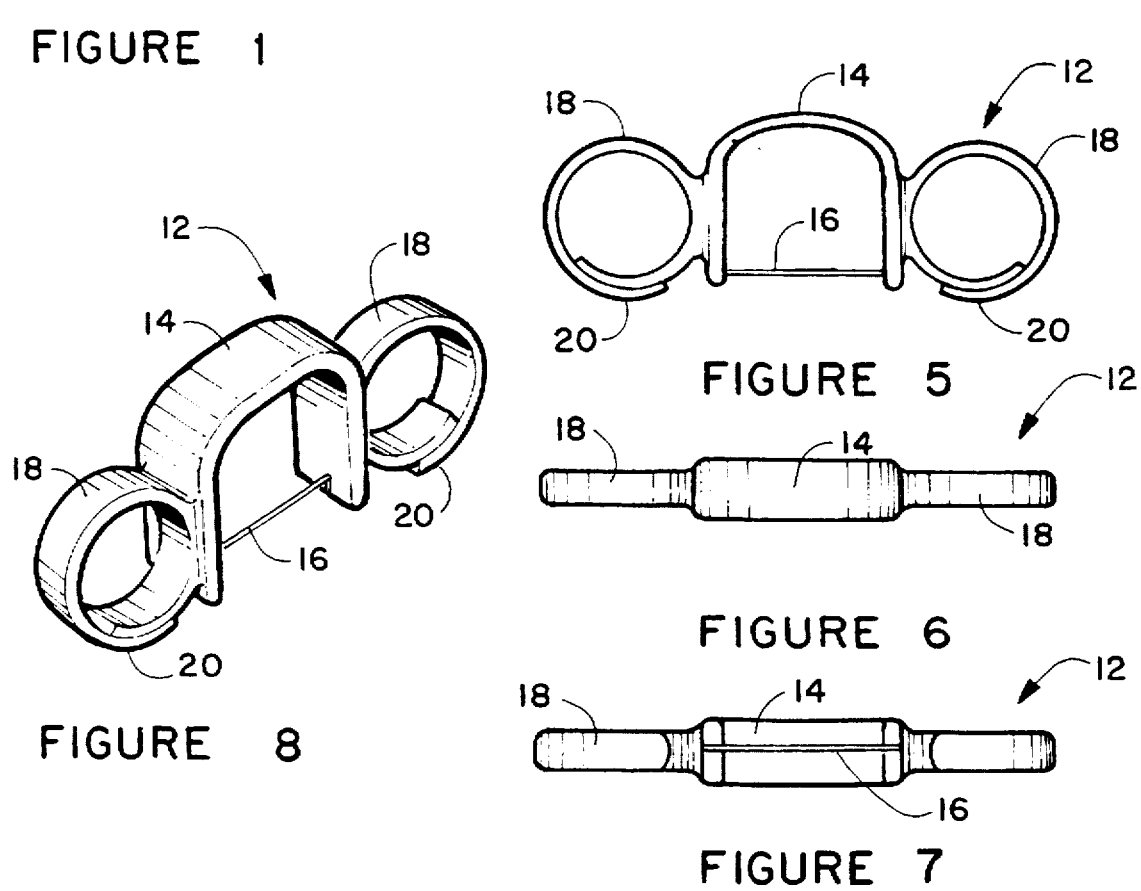

5,893,379

1

DENTAL FLOSSING DEVICE

FIELD OF THE INVENTION

This invention relates to a device useful in supporting dental floss for manually moving floss between the teeth.

BACKGROUND OF THE INVENTION

Flossing, in which a strand of dental floss is moved into and around the space between adjacent teeth has long been recommended by dentists. Conventionally, a strand of floss is wrapped around the middle of each hand, providing a short tensioned length of floss between the fingers. The fingers and floss are inserted into the mouth and the floss is guided between pairs of adjacent teeth.

In order to maintain the floss in position around the fingers and the proper tension on the inter finger strand, the floss must be wrapped tightly around the fingers. The tight wrap of =very thin floss tends to dig into the fingers and become rapidly painful, often limiting the time and care spent in flossing.

Many people find that manipulating the floss while maintaining tension and moving from tooth to tooth while looking at a reverse mirror image to be very difficult. Further the normal gag reflex can be easily triggered while flossing the back molars and touching the palate, much to the user's discomfort.

A number of different flossing devices have been developed in attempts to overcome these problems inherent in manual flossing. Zuehlsdorf in U.S. Pat. No. 5,222,510 discloses a generally U-shaped device in which floss is secured across the ends of the "U" legs and a finger is inserted between the legs. While effective with the front teeth, attempts to floss molars will be difficult since the device can easily rotate about the single finger and not correctly position the floss for entry between adjacent teeth.

Wang describes a flossing system in U.S. Pat. No. 5,503,168 in which two thimble-like members are fitted over two finger tips and floss is wrapped around the two members. While this arrangement avoids the sometimes painful direct wrapping of floss around the fingertips, it has the other problems of the manual fingertip approach. Adjusting the floss length is difficult and slipping of floss on the two members is likely. In addition, two widely spaced fingers must be inserted into the mouth and manipulated.

A large, flexible U-shaped device having floss extending around the "U" and across the space between the ends of the legs is described by Yafai in U.S. Pat. No. 4,304,246. While the endless loop of floss eliminates the risk of floss slipping off of a winding, such as around a finger tip, it the "U" legs are squeezed together at all the floss will fall off the leg ends. Further, the size of the device is such that flossing the back molars will be difficult.

Long lengths of floss secured to widely spaced rings (Trecker, U.S. Pat. No. 4,034,770) or widely spaced tubes (Wei et al, U.S. Pat. No. 5,570,710) may help prevent slipping of the floss ends in use, but still require manual manipulation of the floss, guided by finger tips.

Other flossing devices, such as that described by Peng in U.S. Pat. No. 5,101,843 have a plastic body with projections to the ends of which a length of floss is permanently fastened. This type of device is easily manipulated by one hand. However, because of the lever action between the gripping point and the flossing point, twisting and bending of the device cannot be easily prevented with a single hand

2 holding an extension on the device and the necessary force and movement of the floss between tightly spaced teeth is difficult and require considerable dexterity.

Thus, there is a continuing need for flossing devices that provide more effective flossing, are simpler to manipulate, can be accurately moved along the back molars and the floss inserted between tightly spaced teeth and is inexpensive to manufacture.

SUMMARY OF THE INVENTION

The above-noted problems, ands others, are overcome by the flossing device of this invention which basically comprises a central arch having two spaced leg ends, a length of floss secured between the leg ends and two finger rings secured to the outside surfaces of the arch legs.

The finger rings may be provided in a single to fit typical fingers, since most finger tips are tapered so that thinner fingers will simply be inserted into the rings a slightly greater distance for a snug fit than would be the case with fingers having greater diameters. If desired, the device could be provided with rings of different diameters for fingers of different diameter ranges. For example, smaller rings might be sold for use by children and larger for adults. Alternatively, the rings may be expandable to fit a variety of fingers while providing mild spring pressure on the finger to aid in holding the rings in place.

The flossing device is preferably formed in one piece from a suitable plastic by processes such as injection molding. The floss would preferably be imbedded across the leg ends during the molding. Alternatively, separate rings, such as metal coil rings, could be provided and imbedded into a plastic arch during molding or by adhesive bonding after shaping the arch portion.

While the flossing device may have any suitable dimensions, for an optimum combination of ease of placement on the finger and thumb or two fingers, ease of flossing, and greatest ease of reaching back molars, a width of from about 1.75 to 3 inches is preferred. The distance between arch legs preferably is about 1.0 to 1.5 inch and an arch height of 0.50 to 1.0 inches is preferred.

It is, therefore, an object to provide a flossing device that provides more complete and thorough flossing of spaces between all pairs of teeth. Another object is to provide a flossing device that is easier and more convenient. A further object is to provide a flossing device that can be easily used with no practice by those having limited manual dexterity. Yet another object is to provide a flossing device that provides balanced forces on both sides of a tooth interface to be flossed.

BRIEF DESCRIPTION OF THE DRAWING

Details of the invention, and of preferred embodiments thereof, will be further understood upon reference to the drawing, wherein:

FIG. 1 is a perspective view of the flossing device in place on a person's fingers;

FIG. 2 is a front elevation view of a first embodiment of the flossing device;

FIG. 3 is a top plan view of the flossing device;

FIG. 4 is a top plan view of a second embodiment of the flossing device;

FIG. 5 is a front elevation view of a third embodiment of the flossing device;

FIG. 6 is a top plan view of the flossing device of FIG. 5;

FIG. 7 is a plan view looking into the arch of the flossing device of FIG. 5; and FIG. 8 is a perspective view of the flossing device of FIG. 5.

DETAILED DESCRIPTION OF PREFERRED EMBODIMENTS

Referring to FIG. 1, there is seen a hand 10 having the flossing device 12 in place on the index finger and thumb. Device 12 may, of course be placed on any desired fingers (including a thumb) of either hand. When a finger is referred to in this application, any of the five fingers on either hand is included. Device 12 includes a central arch 14 with floss 16 secured firmly between the ends of the arch legs. Any conventional floss may be used. The floss may be a strand or tape and is preferably a shed resistant material. Two rings 18 are secured to the arch legs on opposite sides. Since finger tips generally gradually widen from the tip back to the first knuckle, a single ring diameter will accommodate most fingers. Of course, devices 12 with rings 18 of different diameters could be provided, e.g., smaller rings for children and larger rings for adults.

FIGS. 2 and 3 detail a first embodiment of device 12. Arch 14 is formed from a suitable plastic. Typical plastics include acrylics, poly vinyl chloride, polyolefins such as polypropylene and polyethylene and cominations thereof. Rings 18 are metal coils, preferably fairly stiff to be shape retaining in use. Floss 16 is embedded in the ends of the legs of arch 14, preferably being taut. Rings 18 are also embedded in the legs. Typically, arch 14 is injection molded in a mold that holds rings 18 and floss 16 extending into the mold sufficiently to produce the desired embediments during molding. If desired, rings 18 and floss 16 could be adhesively bonded to arch 14 after molding of arch 14.

While positioning rings 18 in the same plane as the plane of arch 14 is very effective, for a closer match to the "V" formed by adjacent fingers as seen in FIG. 1, rings 18 could be secured to arch 14 with the planes of the rings each lying at an angle of up to about 20° to the plane of the arch as shown in FIG. 4.

A second embodiment of the flossing device is illustrated in FIGS. 5–8. Here, arch 14 and rings 18 are formed as a single, unitary structure. Floss 16 is preferably embedded in the ends of the arch legs during molding of the device, although adhesive or melt bonding could be used if desired.

For the maximum adaptability of rings 18 to fingers of different circumference, rings 18 in the embodiment of FIGS. 58 have a divided segment 20 along the circumference, with overlapping portions that produce a complete ring of variable circumference. Preferably, the entire assembly is injection molded in a mold that can in a conventional manner provide the divided segments 20 and can hold floss 16 taut in position for embediment in leg ends of arch 14. As with the embodiment of FIG. 4, the planes of rings 18 can be formed in the same plane as that of arch 14 or at an angle of up to about 20° relative to that plane.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A single-use flossing device which comprises:

a generally U-shaped central arch formed from a plastic material;

said U-shaped central arch having two generally parallel leg portions, having spaced inner leg portion sides and outer leg portion sides;

a length of dental floss extending between said distal ends and tautly embedded in said inner leg portion sides;

a ring secured to each of said outer leg portion sides adjacent to said distal leg ends;

each said ring being divided and overlapping for receiving and accommodating fingers of different diameters.

2. The flossing device according to claim 1 wherein said rings are larger than a finger tip of an average hand and smaller than the distal knuckle of an average hand.

3. The flossing device according to claim 1 wherein said rings are wire coils that are partially embedded in said legs.

4. The flossing device according to claim 1 wherein said arch lies in one plane and said rings lie on planes at an angle of 0 to 20° to said arch plane.

5. The single-use flossing device according to claim 1 wherein said U-shaped arch and said rings are a one piece molded plastic unit.

6. A single-use flossing device which comprises:

a generally U-shaped central arch formed from a plastic material;

said U-shaped central arch having two generally parallel leg portions, having juxtaposed inner leg portion sides and outer leg portion sides;

a length of dental floss extending between said distal ends and tautly embedded in said inner leg portion sides;

a plastic ring portion on each said outer leg portion side adjacent to each said distal leg end;

said plastic ring portions and U-shaped central arch lying on approximately the same plane;

said U-shaped central arch and said ring portions forming a one-piece plastic molded unit;

each said ring portion being divided and overlapping for receiving and accommodating fingers of different diameters.

* * * * *